United States Patent [19]
Wellems et al.

[11] Patent Number: 5,476,785
[45] Date of Patent: Dec. 19, 1995

[54] RECOMBINANT DNA CLONE CONTAINING A GENOMIC FRAGMENT OF PFHRP-II GENE FROM *PLASMODIUM FALCIPARUM*

[75] Inventors: Thomas E. Wellems, Rockville; Russell J. Howard, Gaithersburg, both of Md.

[73] Assignee: The United States of America as represented by the Department of Health and Human Services, Washington, D.C.

[21] Appl. No.: 161,406

[22] Filed: Dec. 6, 1993

Related U.S. Application Data

[62] Division of Ser. No. 791,392, Nov. 14, 1991, Pat. No. 5,296,382, which is a division of Ser. No. 518,299, May 3, 1990, Pat. No. 5,130,416, which is a continuation of Ser. No. 279,245, Dec. 1, 1988, abandoned, which is a division of Ser. No. 895,942, Aug. 13, 1986, abandoned.

[51] Int. Cl.$^6$ .............................. C12N 1/21; C12N 15/30; C12N 15/70; C07K 14/445
[52] U.S. Cl. ................. 435/252.3; 435/69.3; 435/252.33; 435/320.1; 530/350; 530/395; 536/23.4; 536/23.5
[58] Field of Search ................................ 435/69.3, 320.1, 435/252.3, 243; 424/88, 184.1, 185.1; 530/395, 388.6; 536/23.1, 23.5

[56] References Cited

U.S. PATENT DOCUMENTS

| | | | |
|---|---|---|---|
| 4,196,265 | 4/1980 | Kopnowski et al. | 435/2 |
| 4,707,445 | 11/1987 | McCutchan et al. | 435/91 |
| 5,001,225 | 3/1991 | Taylor | 530/387 |
| 5,130,416 | 7/1992 | Wellems et al. | 530/350 |
| 5,296,382 | 3/1994 | Wellems et al. | 436/501 |

OTHER PUBLICATIONS

Proc.Natl.Acad.Sci. USA, vol. 83, pp. 6065–6069 Aug. 1986.
Aley, S. B., et al., J. Exp. Med. 160:1585–1590 (1984), "Knob–positive and knob–negative *Plasmodium falciparum* differ in expression of a strain–specific malarial ant the surface of infected erythrocytes".
Bellou, et al., Science 228:996–999 (1985), "Immunogenicity of synthetic peptide form circumsporozoite protein".
Dame, J. B., et al., Science 225:593–599 (1984), "Structure of the gene encoding the immunodominant surface antigen on the sporozoite of the human malaria parasite *Plasmodium falciparum*".
Leech, J. R., et al., J. Cell Biology 98:1256–1264 (Apr., 1984), "*Plasmodium falciparum* malaria: association of knobs on the surface of infected erythrocytes with a histidine–rich protein and the erythrocyte skeleton".
McCutchan, T. F. et al., Science 225:625–628 (1984), "Mung bean nuclease cleaves Plasmodium genomic DNA at sites before and after genes".
Stahl, H. D., et al., Nucleic Acids Res. 13:7837–7846 (1985), "Sequence of a cDNA encoding a small polymorphic histidine– and alanine–rich protein from *Plasmodium falciparum*".
Wellems, T. E., et al., *Molecular strategies of parasitic invasion* (1987, Alan R. Liss, Inc., pp. 47–58, "Histidine–rich proteins in *Plasmodium falciparum*:an update and perspective."

*Primary Examiner*—Thomas M. Cunningham
*Attorney, Agent, or Firm*—Birch, Stewart, Kolasch & Birch

[57] ABSTRACT

The invention relates to isolated clones of DNA from *Plasmodium falciparum* that encode a histidine-rich protein from that organism. The PfHRPII protein is expressed in *P. falciparum*-infected erythrocytes. The cloned gene segment includes an intron-exon boundary near the amino-terminus of the coding sequence. The PfHRPII protein has a Mr of 60–80 kDa as determined by SDS-PAGE. This is substantially higher than the molecular weight of about 35 kDa as estimated from the predicted amino acid sequence of PfHRPII. The PfHRPII amino acid sequence includes a hydrophobic leader sequence, consistent with secretion of PfHRPII observed in vivo and in vivo. The amino acid sequence of PfHRPII is also characterized by a number of tandem repeats having a high content of histidine, alanine and aspartic acid.

11 Claims, 4 Drawing Sheets

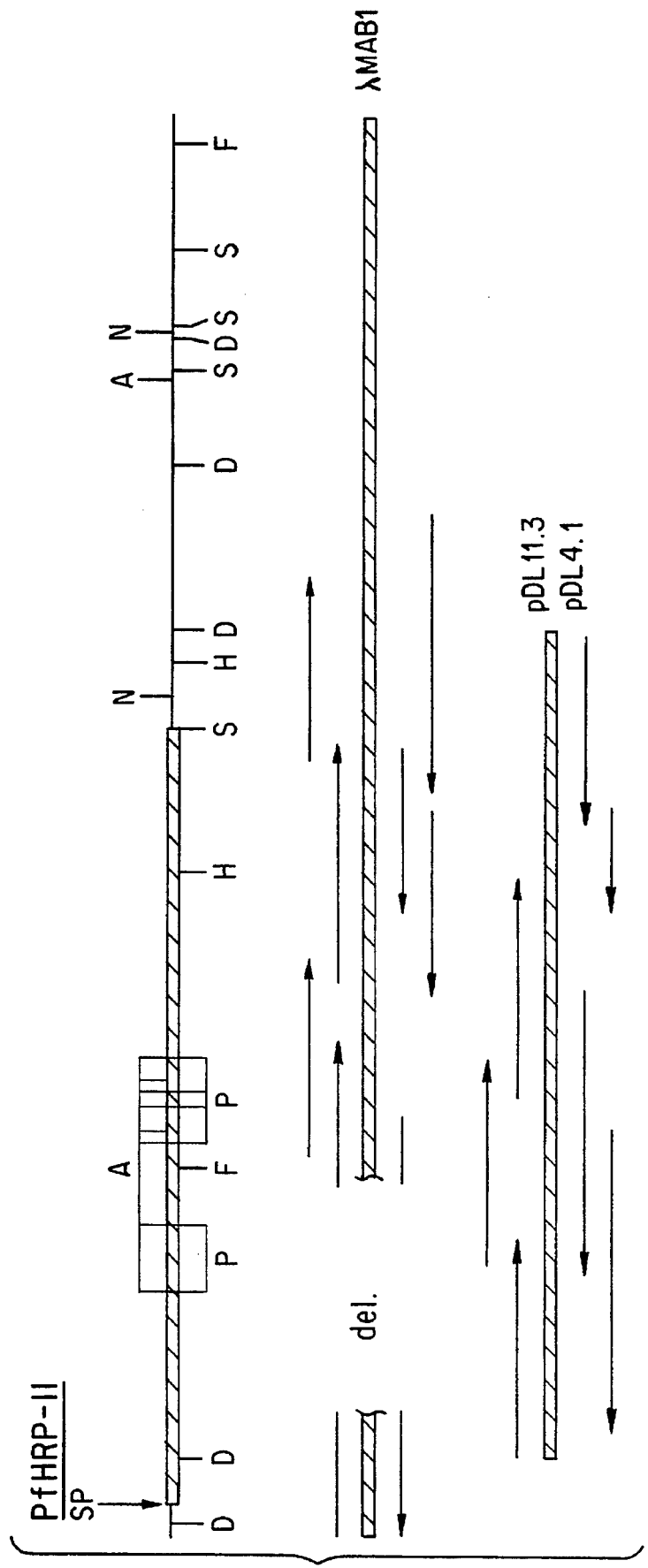
FIG. 1
FIG. 3

```
                                        Intron  ⟵ Asn Asn Ser Ala
                    TAAATTTTTTCATTTTTAAATGCTTTTTTATTTTTATATAG AAT AAT TCC GCA   53

Phe Asn Asn Asn Leu Cys Ser Lys Asn Ala Lys Cly Leu Asn Leu Asn Lys Arg Leu Leu
TTT AAT AAT AAC TTG TGT AGC AAA AAT GCA AAA GGA CTT AAT TTA AAT AAG AGA TTA TTA  113

His Glu Thr Gln Ala His Val Asp Asp Ala His His Ala His His Val Ala Asp Ala His
CAC GAA ACT CAA GCA CAT GTA GAT GAT GCC CAT CAT GCT CAT CAT GTA GCC GAT GCC CAT  173

His Ala His His Ala His His Ala Ala Asp Ala His His Ala His His Ala Ala Asp Ala
CAT GCT CAT CAT GCT CAC CAT GCA GCC GAT GCC CAT CAC GCT CAT CAT GCA GCC GAT GCT  233

His His Ala His His Ala Ala Asp Ala His His Ala His His Ala Ala Asp Ala His His
CAT CAT GCT CAC CAT GCA GCC GAT GCC CAT CAC GCT CAT CAT GCA GCC GAT GCC CAT CAT  293

Ala His His Ala Ala Asp Ala His His Ala His His Ala Ala Asp Ala His His Ala His
GCT CAC CAT GCA GCT GAT GCT CAT CAC GCT CAT CAT GCA GCC GAT GCC CAT CAT GCT CAT  353

His Ala Ala Asp Ala His His Ala His His Ala Ala Asp Ala His His Ala His His Ala
CAT GCA GCC GAT GCC CAT CAT GCT CAC CAT GCA GCT GAT GCT CAT CAC GCT CAT CAT GCA  413

Ala Asp Ala His His Ala His His Ala Ala Tyr Ala His His Ala His His Ala Ser Asp
GCC GAT GCC CAT CAT GCT CAT CAT GCA GCC TAT GCC CAT CAT GCT CAT CAT GCA TCC GAT  473

Ala His His Ala Ala Asp Ala His His Ala Ala Tyr Ala His His Ala His His Ala Ala
GCT CAT CAT GCA GCT GAT GCT CAC CAT GCA GCT TAT GCC CAT CAC GCT CAT CAT GCA GCT  533

Asp Ala His His Ala Ala Asp Ala His His Ala Ala Tyr Ala His His Ala His His Ala
GAT GCT CAT CAT GCA GCT GAT GCT CAC CAT GCA GCT TAT GCC CAT CAC GCT CAT CAT GCA  593

Ala Asp Ala His His Ala Ala Asp Ala His His Ala Thr Asp Ala His His Ala His His
GCT GAT GCT CAT CAT GCA GCC GAT GCT CAC CAT GCA ACC GAT GCT CAT CAC GCT CAC CAT  653

Ala Ala Asp Ala His His Ala Thr Asp Ala His His Ala Ala Asp Ala His His Ala Ala
GCA GCC GAT GCT CAC CAT GCA ACC GAT GCT CAT CAT GCA GCC GAT GCT CAC CAT GCA GCC  713
```

FIG.2A

```
Asp Ala His His Ala Thr Asp Ala His His Ala Ala Asp Ala His His Ala Thr Asp Ala
GAT GCT CAT CAT GCA ACC GAT GCT CAT CAT GCA GCC GAT GCT CAC CAT GCA ACC GAT GCT   773

His His Ala Ala Asp Ala His His Ala Ala Asp Ala His His Ala Thr Asp
CAT CAT GCA GCC GAT GCT CAC CAT GCA GCC GAT GCT CAC CAT GCA ACC GAT — — —   824

Ser His His           Ala His His Ala Ala Asp Ala His His Ala
— — — — —   TCT CAT CAC — —       GCT CAC CAT GCA GCC GAT GCT CAT CAT GCA   863

Ala Ala His His Ala Thr Asp Ala His His Ala Ala Ala His His Ala Thr Asp Ala His
GCC GCA CAC CAT GCA ACT GAT GCT CAC CAT GCA GCC GCA CAC CAT GCA ACC GAT GCT CAC   923

His Ala Ala Ala His His                  Glu Ala Ala Thr His Cys Leu Arg His
CAT GCA GCC GCA CAC CAC — — — — — —      GAA GCC GCC ACA CAT TGC CTA CGC CAT     968

End
TAAATTTATTTAATAATAGATTAAAAATATTATAAAAATAAAAACATAAACACAGAAATTACAAAAAAAATACATATGA  1047

ATTTTTTTTTGTAATCTTCCTTATAAATATAGAATAATGAATCATATAAAACATATCATTATTCATTTATTTACATTT  1126

AAAATTATTGTTTCAGTATCTTTA                                                         1150
```

FIG.2A(cont.)

```
                                          Met Val Ser Phe Ser Lys Asn
                      UAAAAUUAUUUAAUAAAA  AUG GUU UCC UUC UCA AAA AAU

Lys Val Leu Ser Ala Ala Val Phe Ala Ser Val Leu Leu Leu Asp Asn Asn Asn Ser Ala
AAA GUA UUA UCC GCU GCC GUU UUU GCC UCC GUA CUU UUG UUA GAU AAC AAU AAU UCC GCA

Phe Asn Asn Asn Leu Cys Ser Lys Asn Ala Lys Gly
UUU AAU AAU AAC UUG UGU AGC AAA AAU GCA AAA GGA
```

FIG.2B

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
      ( A ) LENGTH: 1150 base pairs
      ( B ) TYPE: nucleic acid
      ( C ) STRANDEDNESS: double
      ( D ) TOPOLOGY: linear ( i i ) MOLECULE TYPE: DNA (genomic)

(vi) ORIGINAL SOURCE:
    (A) ORGANISM: Plasmodium falciparum (ix) FEATURE:
    (A) NAME/KEY: exon
    (B) LOCATION: 42..968

(ix) FEATURE:
    (A) NAME/KEY: CDS
    (B) LOCATION: 42..968
    (D) OTHER INFORMATION: /product="Plasmodium falciparum Histidine Rich Protein"

(ix) FEATURE:
    (A) NAME/KEY: intron
    (B) LOCATION: 1..41

(xi) SEQUENCE DESCRIPTION: SEQ ID NO:1:

```
TAAATTTTTT CATTTTAAA TGCTTTTTA TTTTATATA G AAT AAT TCC GCA                53
                                          Asn Asn Ser Ala
                                           1

TTT AAT AAT AAC TTG TGT AGC AAA AAT GCA AAA GGA CTT AAT TTA AAT         101
Phe Asn Asn Asn Leu Cys Ser Lys Asn Ala Lys Gly Leu Asn Leu Asn
 5               10                  15                  20

AAG AGA TTA TTA CAC GAA ACT CAA GCA CAT GTA GAT GAT GCC CAT CAT         149
Lys Arg Leu Leu His Glu Thr Gln Ala His Val Asp Asp Ala His His
             25                  30                  35

GCT CAT CAT GTA GCC GAT GCC CAT CAT GCT CAT CAT GCT CAC CAT GCA         197
Ala His His Val Ala Asp Ala His His Ala His His Ala His His Ala
         40                  45                  50

GCC GAT GCC CAT CAC GCT CAT CAT GCA GCC GAT GCT CAT CAT GCT CAC         245
Ala Asp Ala His His Ala His His Ala Ala Asp Ala His His Ala His
     55                  60                  65

CAT GCA GCC GAT GCC CAT CAC GCT CAT CAT GCA GCC GAT GCC CAT CAT         293
His Ala Ala Asp Ala His His Ala His His Ala Ala Asp Ala His His
 70                  75                  80

GCT CAC CAT GCA GCT GAT GCT CAT CAC GCT CAT CAT GCA GCC GAT GCC         341
Ala His His Ala Ala Asp Ala His His Ala His His Ala Ala Asp Ala
 85                  90                  95                 100

CAT CAT GCT CAT CAT GCA GCC GAT GCC CAT CAT GCT CAC CAT GCA GCT         389
His His Ala His His Ala Ala Asp Ala His His Ala His His Ala Ala
                105                 110                 115

GAT GCT CAT CAC GCT CAT CAT GCA GCC GAT GCC CAT CAT GCT CAT CAT         437
Asp Ala His His Ala His His Ala Ala Asp Ala His His Ala His His
    120                 125                 130

GCA GCC TAT GCC CAT CAT GCT CAT CAT GCA TCC GAT GCT CAT CAT GCA         485
Ala Ala Tyr Ala His His Ala His His Ala Ser Asp Ala His His Ala
        135                 140                 145

GCT GAT GCT CAC CAT GCA GCT TAT GCC CAT CAC GCT CAT CAT GCA GCT         533
Ala Asp Ala His His Ala Ala Tyr Ala His His Ala His His Ala Ala
    150                 155                 160

GAT GCT CAT CAT GCA GCT GAT GCT CAC CAT GCA GCT TAT GCC CAT CAC         581
Asp Ala His His Ala Ala Asp Ala His His Ala Ala Tyr Ala His His
165                 170                 175                 180

GCT CAT CAT GCA GCT GAT GCT CAT CAT GCA GCC GAT GCT CAC CAT GCA         629
Ala His His Ala Ala Asp Ala His His Ala Ala Asp Ala His His Ala
                185                 190                 195

ACC GAT GCT CAT CAC GCT CAC CAT GCA GCC GAT GCT CAC CAT GCA ACC         677
Thr Asp Ala His His Ala His His Ala Ala Asp Ala His His Ala Thr
            200                 205                 210

GAT GCT CAT CAT GCA GCC GAT GCT CAC CAT GCA GCC GAT GCT CAT CAT         725
Asp Ala His His Ala Ala Asp Ala His His Ala Ala Asp Ala His His
        215                 220                 225
```

| | | | | | | | | | | | | | | | | |
|---|---|---|---|---|---|---|---|---|---|---|---|---|---|---|---|---|
| GCA | ACC | GAT | GCT | CAT | CAT | GCA | GCC | GAT | GCT | CAC | CAT | GCA | ACC | GAT | GCT | 773 |
| Ala | Thr 230 | Asp | Ala | His | His | Ala 235 | Ala | Asp | Ala | His | His 240 | Ala | Thr | Asp | Ala | |
| CAT | CAT | GCA | GCC | GAT | GCT | CAC | CAT | GCA | GCC | GAT | GCT | CAC | CAT | GCA | ACC | 821 |
| His 245 | His | Ala | Ala | Asp | Ala 250 | His | His | Ala | Ala | Asp 255 | Ala | His | His | Ala | Thr 260 | |
| GAT | TCT | CAT | CAC | GCT | CAC | CAT | GCA | GCC | GAT | GCT | CAT | CAT | GCA | GCC | GCA | 869 |
| Asp | Ser | His | His 265 | Ala | His | His | Ala | Ala | Asp 270 | Ala | His | His | Ala | Ala 275 | Ala | |
| CAC | CAT | GCA | ACT | GAT | GCT | CAC | CAT | GCA | GCC | GCA | CAC | CAT | GCA | ACC | GAT | 917 |
| His | His | Ala | Thr 280 | Asp | Ala | His | His | Ala 285 | Ala | Ala | His | His | Ala 290 | Thr | Asp | |
| GCT | CAC | CAT | GCA | GCC | GCA | CAC | CAC | GAA | GCC | GCC | ACA | CAT | TGC | CTA | CGC | 965 |
| Ala | His | His 295 | Ala | Ala | Ala | His | His 300 | Glu | Ala | Ala | Thr | His 305 | Cys | Leu | Arg | |
| CAT | TAAATTTATT | TAATAATAGA | TTAAAAATAT | TATAAAAATA | AAAACATAAA | | | | | | | | | | | 1018 |
| His | | | | | | | | | | | | | | | | |
| CACAGAAATT | ACAAAAAAAA | TACATATGAA | TTTTTTTTTT | GTAATCTTCC | TTATAAATAT | | | | | | | | | | | 1078 |
| AGAATAATGA | ATCATATAAA | ACATATCATT | ATTCATTTAT | TTACATTTAA | AATTATTGTT | | | | | | | | | | | 1138 |
| TCAGTATCTT | TA | | | | | | | | | | | | | | | 1150 |

( 2 ) INFORMATION FOR SEQ ID NO:2:

( i ) SEQUENCE CHARACTERISTICS:
        ( A ) LENGTH: 309 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Asn 1 | Asn | Ser | Ala | Phe 5 | Asn | Asn | Asn | Leu | Cys 10 | Ser | Lys | Asn | Ala | Lys 15 | Gly |
| Leu | Asn | Leu | Asn 20 | Lys | Arg | Leu | Leu | His 25 | Glu | Thr | Gln | Ala | His 30 | Val | Asp |
| Asp | Ala | His 35 | His | Ala | His | His | Val 40 | Ala | Asp | Ala | His | His 45 | Ala | His | His |
| Ala | His 50 | His | Ala | Ala | Asp | Ala 55 | His | His | Ala | His | His 60 | Ala | Ala | Asp | Ala |
| His 65 | His | Ala | His | His | Ala 70 | Ala | Asp | Ala | His | His 75 | Ala | His | His | Ala | Ala 80 |
| Asp | Ala | His | His | Ala 85 | His | His | Ala | Ala | Asp 90 | Ala | His | His | Ala | His 95 | His |
| Ala | Ala | Asp | Ala 100 | His | His | Ala | His 105 | His | Ala | Ala | Asp | Ala 110 | His | His | Ala |
| His | His | Ala 115 | Ala | Asp | Ala | His | His 120 | Ala | His | His | Ala | Ala 125 | Asp | Ala | His |
| His | Ala 130 | His | His | Ala | Ala | Tyr 135 | Ala | His | His | Ala | His 140 | His | Ala | Ser | Asp |
| Ala 145 | His | His | Ala | Ala | Asp 150 | Ala | His | His | Ala | Ala 155 | Tyr | Ala | His | His | Ala 160 |
| His | His | Ala | Ala | Asp 165 | Ala | His | His | Ala | Ala 170 | Asp | Ala | His | His | Ala 175 | Ala |
| Tyr | Ala | His | His 180 | Ala | His | His | Ala | Ala 185 | Asp | Ala | His | His 190 | Ala | Ala | Asp |
| Ala | His | His | Ala | Thr | Asp | Ala | His | His | Ala | His | His | Ala | Ala | Asp | Ala |

-continued

```
                195                              200                              205
His His Ala Thr Asp Ala His His Ala Ala Asp Ala His His Ala Ala
    210                     215                     220

Asp Ala His His Ala Thr Asp Ala His His Ala Ala Asp Ala His His
225                     230                     235                         240

Ala Thr Asp Ala His His Ala Ala Asp Ala His His Ala Ala Asp Ala
                245                     250                     255

His His Ala Thr Asp Ser His His Ala His His Ala Ala Asp Ala His
            260                     265                     270

His Ala Ala Ala His His Ala Thr Asp Ala His His Ala Ala Ala His
    275                     280                     285

His Ala Thr Asp Ala His His Ala Ala Ala His His Glu Ala Ala Thr
    290                     295                     300

His Cys Leu Arg His
305
```

( 2 ) INFORMATION FOR SEQ ID NO:3:

( i ) SEQUENCE CHARACTERISTICS:
        ( A ) LENGTH: 135 base pairs
        ( B ) TYPE: nucleic acid
        ( C ) STRANDEDNESS: single
        ( D ) TOPOLOGY: linear ( i i ) MOLECULE TYPE: mRNA ( v i ) ORIGINAL SOURCE:
        ( A ) ORGANISM: Plasmodium falciparum ( i x ) FEATURE:
        ( A ) NAME/KEY: exon
        ( B ) LOCATION: 19..135
        ( D ) OTHER INFORMATION: /product="Pf Histidine Rich
            Protein ___ Amino Terminus"

( i x ) FEATURE:
        ( A ) NAME/KEY: 5'UTR
        ( B ) LOCATION: 1..18

( i x ) FEATURE:
        ( A ) NAME/KEY: CDS
        ( B ) LOCATION: 19..135
        ( D ) OTHER INFORMATION: /product="Plasmodium falciparum
            Histidine Rich Protein"

( x i ) SEQUENCE DESCRIPTION: SEQ ID NO:3:

```
UAAAAUUAUU UAAUAAAA AUG GUU UCC UUC UCA AAA AAU AAA GUA UUA UCC      51
                    Met Val Ser Phe Ser Lys Asn Lys Val Leu Ser
                     1               5                      10

GCU GCC GUU UUU GCC UCC GUA CUU UUG UUA GAU AAC AAU AAU UCC GCA      99
Ala Ala Val Phe Ala Ser Val Leu Leu Leu Asp Asn Asn Asn Ser Ala
            15                      20                  25

UUU AAU AAU AAC UUG UGU AGC AAA AAU GCA AAA GGA                     135
Phe Asn Asn Asn Leu Cys Ser Lys Asn Ala Lys Gly
            30                  35
```

( 2 ) INFORMATION FOR SEQ ID NO:4:

( i ) SEQUENCE CHARACTERISTICS:
        ( A ) LENGTH: 39 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

-continued

```
Met  Val  Ser  Phe  Ser  Lys  Asn  Lys  Val  Leu  Ser  Ala  Ala  Val  Phe  Ala
 1              5                         10                         15

Ser  Val  Leu  Leu  Leu  Asp  Asn  Asn  Asn  Ser  Ala  Phe  Asn  Asn  Asn  Leu
               20                        25                         30

Cys  Ser  Lys  Asn  Ala  Lys  Gly
          35
```

(2) INFORMATION FOR SEQ ID NO:5:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (v) FRAGMENT TYPE: internal (ix) FEATURE:
        (A) NAME/KEY: Peptide
        (B) LOCATION: 1..15
        (D) OTHER INFORMATION: /label=peptide
        / note="synthetic peptide used to produce
        anti-PfHRP- II antiserum"

(xi) SEQUENCE DESCRIPTION: SEQ ID NO:5:

```
Ala  His  His  Ala  His  His  Ala  Ala  Asp  Ala  His  His  Ala  Ala  Asp
 1              5                        10                         15
```

RECOMBINANT DNA CLONE CONTAINING A GENOMIC FRAGMENT OF PFHRP-II GENE FROM *PLASMODIUM FALCIPARUM*

This application is a divisional of application Ser. No. 07/791,392, filed on Nov. 14, 1991, issued as U.S. Pat. No. 5,296,382, the entire contents of which are hereby incorporated by reference, which in turn is a divisional of Ser. No. 07/518,299 filed May 3, 1990 and issued as U.S. Pat. No. 5,130,416, which in turn is a continuation of Ser. No. 07/279,245 filed Dec. 1, 1988, now abandoned, which is a divisional of Ser. No. 06/895,942 filed Aug. 13, 1986, now abandoned.

BACKGROUND OF THE INVENTION

1. Technical Field

The present invention is related to malarial antigens and the genes encoding the same. More particularly, the present invention is related to a recombinant DNA clone (pDL4.1) containing a genomic fragment of PfHRP-II gene from *Plasmodium falciparum*.

2. State of the Art

Of various parasitic diseases, malaria remains one of the most menacing conditions. Substantial progress has been made in identifying the pathogenic factors causing malaria and *Plasmodium falciparum* has been recognized as the major pathogen of human malarial disease.

Recent advances in biochemical, immunological and genetic technologies have led to the recognition of certain antigens and to the characterization of certain genes or gene-fragments encoding the synthesis of malarial pathogenic antigens. The present invention relates to one such discovery.

SUMMARY OF INVENTION

An object of the present invention is to provide a new, soluble, histidine-rich protein, designated PfHRPII, from *P. falciparum* infected erythrocytes.

A further object of the present invention is to provide a recombinant DNA clone containing a genomic fragment capable of encoding PfHRP-II protein.

A still further object of the present invention is to provide a method of early detection or diagnosis of malarial infection employing the PfHRP-II antigen or an antibody having specificity against said PfHRP-II antigen.

It is another object of the present invention to provide a pharmaceutical composition comprising immunogenic amount of PfHRP-II to induce protective immunity in a host to which said pharmaceutical composition is administered in a pharmaceutically acceptable vehicle or carrier.

Other objects and advantages will become evident as the detailed description of the invention proceeds.

BRIEF DESCRIPTION OF DRAWINGS

These and other objects, features and many of the attendant advantages of the invention will be better understood upon a reading of the following detailed description when considered in connection with the accompanying drawings wherein:

FIG. 1 shows the genomic map and sequencing strategy for PfHRP-II. Coding regions are directed from left to right and are marked by heavy lines on the genomic maps. Comparison of the Alu I and Dra I restriction fragments from genomic DNA with those from λMAB1 revealed a 279 bp deletion occurring within the region of tandem repeats but the reading frame having been preserved. Restriction patterns of inserts from clones pDL4.1 and pDL11.3 were compared with corresponding restriction digests of genomic DNA by Southern blotting and showed no evidence of deletion or rearrangement. Nucleotide sequence analysis was performed on subclones in M13mp18 having targeted deletions generated by timed exonuclease III digestions. The coding strand of the pDS11.1 insert was determined from fragments digested with Pvu II and subcloned into M13mp19. Sp, splice site at 3' end of intron. A, Alu I; D, Dra I; F, Fok I; H, Hinf I; N, Nde I; P, Pvu II; S, Ssp I;

FIG. 2 (A) [SEQ. ID. NO. :1] shows the genomic and deduced amino acid sequences of PfHRP-II displayed by automated plotting. The register of the open reading frame of PfHRP-II is in phase with the gene for β-galactosidase in λMAB1 as expected, since this clone produces a fusion protein reacting with both McAb87 and anti-β-galactosidase. The sequence shown for PfHRP-II does not include the nucleotides added by ligation of Eco RI linkers (GGAATTCC) to the genomic fragment during library construction.

FIG. 2(B) [SEQ. ID. NO. :3] shows the sequence of PfHRP-II mRNA obtained by primer extension analysis. The splice junction is indicated by the arrow. The hydrophobic leader sequence is underlined;

FIG. 3 shows the schematic representation of the gene for PfHRP-II. The lengths of the coding regions, represented by boxes, are drawn to scale. Intervening sequences (I) and repeat domains ($R_{II}$) are shown.

DETAILED DESCRIPTION OF INVENTION

Figure 4:
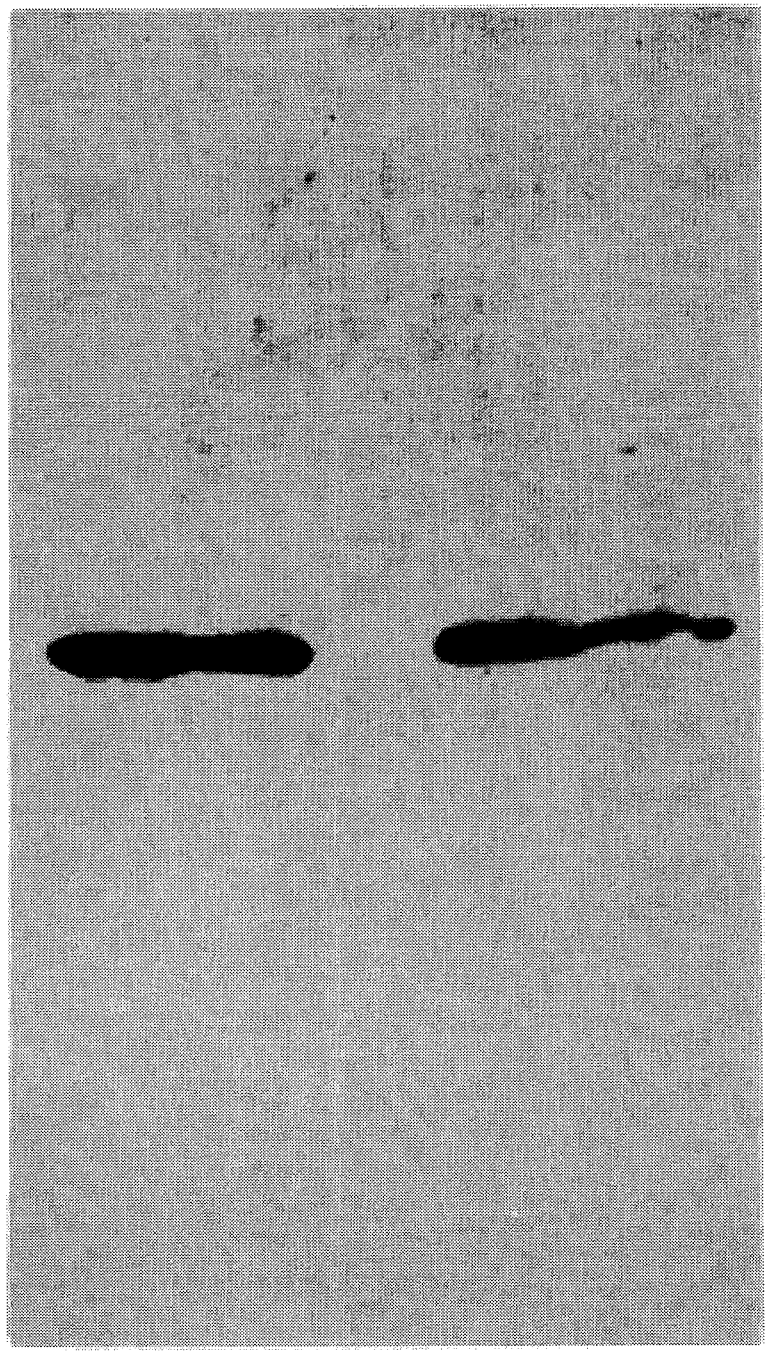
FIG. 4 shows immunoprecipitation of PfHRP-II from infected culture supernatant with McAb87 (identified in FIG. 4 as M87) and rabbit antiserum (identified in FIG. 4 as RαP) to the synthetic oligopeptide AHH(AHHAAD)$_2$ [SEQ. ID. NO. :5]. The PfHRP-II is labelled with $^3$H-alanine[A] and $^3$H-histidine[H] but not with $^3$H-isoleucine[I].

The above and various other objects and advantages of the present invention are achieved by a recombinant DNA clone (pDL4.1) containing a genomic fragment of the PfHRP-II gene from *P. falciparum*.

Unless defined otherwise, all technical or scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

The term "PfHRP-II" as used herein means a protein whose amino acid sequence and encoding genetic map (nucleotide sequence) are shown in FIG. 2A.

A. Methods of Isolation and Characterization of the Clone

1. A genomic expression library in the vector λAgt11 was constructed from *Plasmodium falciparum* DNA digested with mung bean nuclease. The description of this library and the methods of construction was the same as described by McCutchan et al. (Science 225:625–628). DNA from the 7G8 clone of the Brazil isolate IMT22 of *P. falciparum* (Burkot et al., Trans. R. Soc. Trop. Med. Hyg., 78:339–341) was used to construct the library.

2. A monoclonal antibody, McAb87, was prepared which reacts specifically with the histidine-rich protein PfHRP-II. The methods of preparation and characterization of McAb87 was the same as described by Howard et al. (J. Cell. Biol., 1986).

3. A recombinant DNA clone (λMAB1) was isolated from the genomic expression library by immunoscreening with McAb87. The methods used in the immunoscreening was the same as described by Young and Davis (Proc. Natl. Acad. Sci. USA, 80:1194–1198; Science, 222:778–782) and Dame et al. (Science 225:593–599). Immunoblot analysis of the recombinant clone showed that λMAB1 produced an inducible fusion protein of approximate Mr 144,000 which reacted with both McAb87 and anti-β-galactosidase.

4. The insert was excised with Eco RI from λMAB1 DNA purified by gel electrophoresis and cloned into the sequencing vector M13mp18 using standard procedures (Maniatis et al., Molecular cloning: A Laboratory Manual, Cold Spring Harbor Laboratory, 1982; Yanish-Perron et al., Gene 33:103–119). Sequence analysis was performed on subclones in M13mp18 having targeted deletions generated by exonuclease III digestion. Sequences were obtained by the dideoxynucleotide method (Sanger et al., Proc. Natl. Acad. Sci. USA, 74:5463–5467) using commercially supplied reagents (Bethesda Research Laboratories, Bethesda, Md.). The sequence revealed a region of tandem repeats extending from nucleotides 148–669 predominantly encoding the oligopeptides AHH and AHHAAD [residues 5–9 of SEQ. ID. NO. :5], wherein A=Alanine; H=Histidine and D=Aspartic acid. Restriction analysis identified a 544 bp fragment which spanned the repeats. This fragment was purified and used to probe DNA transfer blots of genomic DNA (Southern, J. Mol. Biol. 98:503). Comparison of the restriction fragments from genomic DNA with those from λMAB1 revealed that a 279 bp deletion had occurred in the repeat region but had preserved the reading frame.

5. To obtain the complete region of tandem repeats in the PfHRP-II gene, P. falciparum DNA was restricted with the enzyme Dra I and ligated into the Sma I site of the plasmid pUC18 using standard methods (Maniatis supra). Two clones, pDL4.1 and pDL11.3, were obtained having identical inserts oriented in opposite direction in the vector. Restriction analysis and comparative DNA transfer blotting were performed as described herein supra and showed no evidence of deletion or rearrangement.

6. RNA transfer blots were performed to confirm that the cloned DNA was transcribed. RNA was isolated from saponin purified P. falciparum parasites suspended in 100 mM NaCl, 10 mM tris pH 8.0, 2 mM $MgCl_2$, 10 mM vanadyl-ribonucleoside comlexes and 1% $NaDodSO_4$. Sequential extraction was carried out with hot phenol and chloroform according to the method of Hyde et al. (Mol. Biochem. Parasitol., 4:283–290). RNA transfer and hybridization with nick-translated pDL4.1 were performed according to the protocols described by Mehdy et al. (Cell 32:763–771).

7. The complete nucleotide sequence of each insert from pDL4.1 and pDL11.3 was determined by the dideoxynucleotide method of Sanger et al, supra, and both were found to be identical. FIGS. 1, 2 and 3 show the map and sequence obtained for the region of the PfHRP-II gene extending from the 3' splice junction of the intron to and through the stop codon.

8. The nucleotide sequence of the RNA transcript extending from the initiating codon to the intron splice junction was obtained by primer extension analysis according to the protocol of Belfort et al. (Cell 41:375–382). Oligonucleotide primers (synthesized as recommended by the manufacturer, Applied Biosystems DNA synthesizer, Foster City, Calif.) were used which were complementary to nucleotides 64–83 and 114–135 of the PfHRP-II genomic sequence (FIG. 2). Reactions were carried out using 0.5 pmol of 5' labelled synthetic oligonucleotide and 10 μg of P. falciparum RNA.

9. To confirm the reading frame and deduced amino acid sequence of PfHRP-II as correct, antisera were generated against a synthetic oligopeptide containing repeats from the deduced sequence and used to immunoprecipitate biosynthetically labelled PfHRP-II. The synthetic oligopeptide AHH(AHHAAD)$_2$ [SEQ. ID. NO. :5] was synthesized by the solid-phase method of Merrifield and Marglin (Ann. Rev. Biochem. 39:841–866) and cleaved from the solid support with liquid HF (Tam et al., J. Am. Chem. Soc. 105:6442–6455). The oligopeptide was desalted using a Biogel P-2 column and coupled to Keyhole Limpet hemocyanin (KLH). Rabbits were immunized with biweekly injections of a 1:1 mixture of the synthetic oligopeptide, AHH(AHHAAD)$_2$, [SEQ. ID. NO. :5] and KLH in Freund's complete adjuvant and antisera were obtained during the 7th week following the first injection. The antiserum thus obtained and McAb87 reacted with specificity with the protein (PfHRP-II) obtained from infected erythrocyte, thus demonstrating the identical nature of the synthetic and the naturally occurring PfHRP-II epitope (FIG. 4). The observed specificity of reaction between the antigen (PfHRP-II) and the antibodies indicates neutralizing efficacy of the antibodies against PfHRP-II.

10. Studies of biosynthetically labelled cultures were performed on the 7G8 clone of P. falciparum maintained in vitro by the methods of Trager and Jensen (Science, 193:673–675). Labelled amino acids L-[2,5-$^3$H]-histidine, L-[2,3-$^3$H]-alanine, L-[4,5-$^3$H]-isoleucine and the labelled sugar D-[6-$^3$H]-galactose were obtained from Amersham Corporation (Arlington Heights, Ill.) and used for biosynthetic labelling according to the procedures of Leech et al. (J. Cell. Biol. 98:1256–1264). Cultures were harvested after 24 hours of labelling and immunoprecipitated by standard methods (Kessler, J. Immunol. 115:1617–1624) using McAb87 and the antisera described in step 9, supra.

A deposit of the recombinant DNA clone (pDL4.1) prepared in accordance with the present invention has been made at the American Type Culture Collection, Rockville, Md. under accession number 40248. It is noted that the deposit made at the ATCC shall be viably maintained for the life of the patent if issued or for at least 30 years from the date of the deposit and made available without restriction to the public upon issuance of the patent, of course, consistent with the provisions of the law.

B. Properties of the PfHRP-II Gene and Expressed Protein

1. The PfHRP-II gene has an interrupted structure, with an intron separating a short (69 bp) exon encoding a hydrophobic leader from a 927 bp exon encoding numerous tandem repeats of very high histidine, alanine and aspartate content (FIGS. 2 and 3).

2. The gene is transcribed to produce an RNA transcript of approximately 2.1 kb.

3. The nucleotide sequence encodes a protein of approximate molecular weight 35,138, a value much lower than the Mr of 60,000–80,000 obtained by SDS-PAGE. Without being bound to any theory, possible explanations for this difference include post-translational events (e.g. dimerization) and anomalous migration during SDS-PAGE.

4. The deduced sequence contains about 34% histidine, 37% alanine and 10% aspartate.

5. PfHRP-II migrates as a multiplet of bands generally spanning 5,000–10,000 Mr which is indicative of post-translational processing.

6. The protein is exported from the parasite into the body fluid. PfHRP-II passes through the host erythrocyte in concentrated "packets" and is released from the infected erythrocyte into the body fluid in vivo or into the culture supernatant in vitro. The mature protein recovered from culture supernatant corresponds to the slowest moving band of the multiplet reactive with McAb87.

7. The mature protein is glycosylated and incorporates radiolabelled galactose.

8. The protein exhibits strong binding to the divalent cations Zn++ and Cu++ (Table 1). Binding of Zn++ to PfHRP-II can be reversed by imidazole, the side group of histidine. Other cations forming chelation complexes with histidine (such as Cd, Hg, Co, Ni) would likewise bind with PfHRP-II.

9. PfHRP-II binds strongly to heparin-Sepharose (Pharmacia) and cannot be eluted by a gradient of NaCl up to 2M NaCl, whereas other proteins which bind to heparin-Sepharose are eluted by $\leq$1.5M NaCl, indicating the polycationic nature of multiple imidazole groups of PfHRP-II.

10. Using McAb87 and/or rabbit antisera, experiments with serum from patients infected with malaria demonstrated the presence of circulating PfHRP-II in infected blood and the presence of antibodies to PfHRP-II in previously infected patients (Data not shown).

11. PfHRP-II has a histidine content that is similar to that of a Mr 30,000 fragment obtained from a histidine-rich glycoprotein (HRG) that has been isolated from normal human serum (Morgan, Biochim. Biophys. Acta. 533:319). HRG interacts with divalent metal ions, heparin, thrombospondin, and autorosette-forming thymocytes. Levels of HRG are decreased in immunosuppressed states indicating that HRG may be linked to immune function. The properties common to PfHRP-II and HRG indicate similarity of the functional role in vivo and that PfHRP-II may alter the physiologic role of HRG.

TABLE 1

| Protein | Binding to column | Peak width (mM imidazole) | Peak max (mM imidazole) |
|---|---|---|---|
| Elution of proteins from $Zn^{2+}$-chelated sepharose 6B by imidazole | | | |
| Bovine serum albumin | − | — | — |
| Human hemoglobin | + | 10-40 | 25 |
| Human transferrin | + | 25-100 | 75 |
| Human α2-macroglobulin | + | 75-130 | 100 |
| Human serum histidine-rich glycoprotein | + | 100-180 | 140 |
| PfHRP-II | + | 260-400 | 325 |
| Elution of PfHRP2 from $Cu^{2+}$-chelated sepharose 6B by imidazole | | | |
| PfHRP-II | + | ND | >450 |

In summary, the amino acid composition and the biochemical and biological properties of the PfHRP-II and its encoding gene clearly distinguish the recombinant clone from any other recombinant heretofore known.

Of course, the malarial antigen of the present invention prepared from the recombinant PfHRP-II clone or synthesized from the known amino acid sequence (FIG. 2) allows the preparation of a pharmaceutical composition comprising immunogenic amount of PfHRP-II to immunize against malaria in a host to whom said pharmaceutical composition is administered in a pharmaceutically acceptable vehicle or carrier such as physiological saline, nontoxic buffers, fillers or adjuvants and the like. Moreover, a kit comprising containers containing antigen and/or antibodies having specificity against PfHRP-II in suitable preservative medium such as physiological saline, nontoxic buffers and the like, and preferably lyophilized or cryopreserved, can be utilized by standard immunological assays, well known in the art, to detect or diagnose even low level or early malarial infection which otherwise cannot be detected by conventional methods such as thin and thick blood smears and the like. The kit may also include such standard items as microtiter plates, micropipettes, agglutination reading means and the like which are normally found in such kits. It is understood that the examples and embodiments described herein are for illustrative purposes only and that various modifications or changes in light thereof will be suggested to persons skilled in the art and are to be included within the spirit and purview of this application and the scope of the appended claims.

We claim:

1. An isolated DNA molecule having a nucleotide sequence that encodes the amino acid sequence of SEQ. I.D. NO. 2.

2. An isolated DNA molecule according to claim 1, having the nucleotide sequence of SEQ. I.D. NO. 1.

3. An isolated DNA molecule comprising nucleotide sequences encoding a polypeptide consisting of amino acid residues 1 through 23 of SEQ. I.D. NO. 4 and amino acid residues 1 through 309 of SEQ. I.D. NO. 2, wherein the amino acid residues of SEQ. I.D. NO. 4 are attached to the amino terminus of the amino acid residues of SEQ. I.D. NO. 2.

4. An isolated recombinant λ phage comprising a DNA molecule according to claim 3.

5. An isolated recombinant λ phage having all of the identifying characteristics of the λ phage clone deposited as ATCC 40248.

6. An isolated recombinant λ phage of claim 5, which is the λ phage deposited as ATCC 40248.

7. An *Escherichia coli* cell containing a plasmid which comprises a DNA molecule according to claim 1.

8. An *Escherichia coli* cell containing a plasmid which comprises a DNA molecule according to claim 2.

9. An *Escherichia coli* cell containing a vector comprising a DNA molecule according to claim 3.

10. An *Escherichia coli* cell containing a λ phage according to claim 4.

11. An *Escherichia coli* cell containing a λ phage according to claim 5.

\* \* \* \* \*